(12) United States Patent
Yano

(10) Patent No.: US 11,554,088 B2
(45) Date of Patent: Jan. 17, 2023

(54) OILY STICK-SHAPED COSMETIC

(71) Applicant: TOKIWA CORPORATION, Nakatsugawa (JP)

(72) Inventor: Hidekazu Yano, Kawaguchi (JP)

( * ) Notice: Subject to any disclaimer, the term of this patent is extended or adjusted under 35 U.S.C. 154(b) by 28 days.

(21) Appl. No.: 17/326,327

(22) Filed: May 21, 2021

(65) Prior Publication Data

US 2021/0369577 A1 Dec. 2, 2021

(30) Foreign Application Priority Data

May 26, 2020 (JP) .............................. JP2020-091113

(51) Int. Cl.
| | |
|---|---|
| *A61K 8/37* | (2006.01) |
| *A61Q 1/10* | (2006.01) |
| *A61Q 19/00* | (2006.01) |
| *A61K 8/36* | (2006.01) |
| *A61K 8/362* | (2006.01) |
| *A61K 8/9789* | (2017.01) |
| *A61K 8/92* | (2006.01) |
| *A61K 8/02* | (2006.01) |

(52) U.S. Cl.
CPC .............. *A61K 8/37* (2013.01); *A61K 8/0229* (2013.01); *A61K 8/361* (2013.01); *A61K 8/362* (2013.01); *A61K 8/922* (2013.01); *A61K 8/9789* (2017.08); *A61Q 1/10* (2013.01); *A61Q 19/001* (2013.01)

(58) Field of Classification Search
None
See application file for complete search history.

(56) References Cited

U.S. PATENT DOCUMENTS

| | | | |
|---|---|---|---|
| 6,132,742 A * | 10/2000 | Le Bras ................... | A61Q 1/04 424/401 |
| 8,580,284 B2 * | 11/2013 | Tamura ................... | A61K 8/731 424/401 |
| 2017/0360666 A1 * | 12/2017 | Pottie .................... | A61K 8/4966 |
| 2018/0140512 A1 * | 5/2018 | Togashi .................. | A61Q 1/08 |
| 2022/0071890 A1 * | 3/2022 | Constantine ........... | A61K 8/375 |
| 2022/0133602 A1 * | 5/2022 | Malvezin ................ | A61Q 1/06 424/401 |

FOREIGN PATENT DOCUMENTS

JP   H6-099284   12/1994

OTHER PUBLICATIONS

FLORAESTERS®30.*

* cited by examiner

*Primary Examiner* — Danah Al-Awadi
(74) *Attorney, Agent, or Firm* — Soei Patent & Law Firm

(57) ABSTRACT

An oily stick-shaped cosmetic containing (A) a partially hydrogenated jojoba ester, (B) Japan wax, (C) a higher fatty acid, and (D) a dimer acid ester.

9 Claims, No Drawings

OILY STICK-SHAPED COSMETIC

CROSS-REFERENCE TO RELATED APPLICATIONS

This application claims the benefit of priority from Japanese Patent Application No. 2020-091113, filed on May 26, 2020, the entire contents of which are incorporated herein by reference.

TECHNICAL FIELD

The present application relates to an oily stick-shaped cosmetic.

BACKGROUND

Oily stick-shaped cosmetics are used as core materials for eyebrow pencils, eyeliner pencils, lip liner pencils, and the like. Since an oily stick-shaped cosmetic is usually produced by extrusion molding or cavity molding, an oil agent is blended in the cosmetic so that it can be molded into a desired core shape. As oil agents adapted to molding, Japan wax, high fatty acids, and the like are used for many oily stick-shaped cosmetics (see, for example, Japanese Examined Patent Publication No. H6-99284).

SUMMARY

In an oily stick-shaped cosmetic having the above-described oil agent blended therein, a so-called blooming phenomenon frequently occurs in which crystals surface over time to turn the surface of the cosmetic white. In the cosmetic causing blooming, not only its external appearance is damaged, but also its usability such as easy drawability is deteriorated. For example, the sensation of the cosmetic being impeded or caught upon the surface of the skin while drawing may be experienced.

Therefore, oily stick-shaped cosmetics may be manufactured to address the above blooming and usability concerns, while having sufficient stability and strength during storage or usage to prohibit the leakage of oily components even at high temperatures as well as to protect against cracking or chipping by impact such as dropping.

Disclosed herein is an example oily stick-shaped cosmetic which may comprise (A) a partially hydrogenated jojoba ester, (B) Japan wax, (C) a higher fatty acid, and (D) a dimer acid ester.

Having the example composition described above, the oily stick-shaped cosmetic does not cause blooming and can have a combination of sufficient strength, storage stability, and usability.

From the viewpoints of suppressing blooming and usability, the component (A) may have a melting point of 45° C. to 55° C.

From the viewpoints of suppressing blooming and securing strength, a sum of contents of the component (A) and the component (D) may be 4% to 10% by mass based on a total amount of the oily stick-shaped cosmetic.

From the viewpoint of suppressing blooming, a mass ratio between the component (A) and the component (D) [component (A)/component (D)] may be 1/6 to 1/1.

From the viewpoint of usability, the oily stick-shaped cosmetic may further comprise a hydrogenated castor oil, and a sum of contents of the component (B) and the component (C) may be 60% to 74% by mass based on a sum of contents of the hydrogenated castor oil, the component (B), and the component (C).

Accordingly, disclosed herein are various examples of an oily stick-shaped cosmetic that does not cause blooming and, at the same time, can have a combination of sufficient strength, storage stability, and usability.

DETAILED DESCRIPTION

Oily Stick-Shaped Cosmetic

An example oily stick-shaped cosmetic comprises a partially hydrogenated jojoba ester (which may also be referred to as component (A)), Japan wax (which may also be referred to as component (B)), a higher fatty acid (which may also be referred to as component (C)), and (a dimer acid ester (which may also be referred to as component (D)). In one or more embodiments, the oily stick-shaped cosmetic may also comprise a powder component and may further comprise an oily component other than those described above.

Component (A) Partially Hydrogenated Jojoba Ester

The partially hydrogenated jojoba ester for use may be an ester oil obtainable by hydrogenating jojoba oil. Examples of the ester oil that may be used include commercially available products such as those sold under FLORAESTERS® 20, FLORAESTERS® 30, and FLORAESTERS® 60 by International Flora Technologies, Ltd.

In one or more embodiments, the component (A) in the oily stick-shaped cosmetic may have a melting point of 45° C. to 55° C., or 50° C. to 55° C., from the viewpoints of suppressing blooming and usability.

The melting point of the component (A) can be measured by the example method that will be described later.

In one or more embodiments, a content of the (A) component in the oily stick-shaped cosmetic, may be 0.1% to 5% by mass, 0.5% to 4.0% by mass, 0.9% to 3.5% by mass, 1.0% to 3.0% by mass, or 1.2% to 2.5% by mass, based on a total mass of the oily stick-shaped cosmetic, from the viewpoints of suppressing blooming, usability and storage stability. In some embodiments, one or more of the aforementioned properties of the cosmetic may be improved by including a content of the (A) component at the smaller example range disclosed above, namely 1.2% to 2.5% by mass.

From the viewpoint of suppressing blooming, a content of the component (A) may be 1% to 8% by mass, or 2% to 5% by mass, based on a total amount of the oily components contained in the oily stick-shaped cosmetic.

Component (B) Japan Wax

Japan wax for use may be one that is used in other cosmetics.

In one or more embodiments, a content of the (B) component in the oily stick-shaped cosmetic may be 5% to 15% by mass, or 8% to 12% by mass, based on a total amount of the oily stick-shaped cosmetic, from the viewpoint of moldability.

Component (C) Higher Fatty Acid

Th higher fatty acid for use may be a fatty acid in which the carbon number of an aliphatic hydrocarbon group (hereinafter, simply referred to as "carbon number") is 12 or more. Examples of the higher fatty acid include myristic acid, palmitic acid, stearic acid, lauric acid, lanolin acid, and behenic acid.

In one or more embodiments, the oily stick-shaped cosmetic may comprise a fatty acid(s) having a carbon number of 20 or less from the viewpoints of easy drawability, particularly absence of stickiness and gentle touch on the skin. The oily stick-shaped cosmetic may comprise a fatty acid(s) having a carbon number of 14 to 20, which may be at least one of myristic acid, palmitic acid, and stearic acid.

In one or more embodiments, a content of the component (C) in the oily stick-shaped cosmetic may be 10% to 40% by mass, or 12% to 20% by mass, based on a total amount of the oily stick-shaped cosmetic, from the viewpoints of moldability and easy drawability.

In some embodiments, a proportion of the fatty acid having a carbon number of 14 to 20 contained in the higher fatty acids having a carbon number of 12 or more may be 50% to 100% by mass, or 70% to 100% by mass, from the viewpoint of gentle touch on the skin.

A mass ratio between the component (B) and the component (C) [component (B)/component (C)] may be 0.25 to 1.4, and from the viewpoint of easy drawability, the mass ratio may be 0.4 to 0.75 or 0.5 to 0.65.

From the viewpoint of usability, the oily stick-shaped cosmetic may further comprise a hydrogenated castor oil. In some embodiments, a sum of contents of the component (B) and the component (C) may be 60% to 74% by mass, or 65% to 72% by mass, based on a sum of contents of the hydrogenated castor oil, the component (B), and the component (C).

Component (D) Dimer Acid Ester

Examples of the dimer acid ester for use may include esters of dimer acid obtained by polymerization of two molecules of unsaturated fatty acids. Examples of the unsaturated fatty acid include linoleic acid, linolenic acid, and oleic acid. Also, examples of the ester moiety of such a dimer acid include ones that may be derived from higher alcohols such as cetyl alcohol, oleyl alcohol, stearyl alcohol, isostearyl alcohol, behenyl alcohol, lauryl alcohol, and linoleyl alcohol; dimer diols obtained by polymerizing two molecules of unsaturated alcohols such as dimer dilinoleyl alcohol; compounds derivable from phytosterol; and castor oil. Specific examples thereof include bisstearyl dimer dilinoleyl dimer dilinoleate, bis(behenyl/isostearyl/phytosteryl) dimer dilinoleyl dimer dilinoleate, hydrogenated castor oil dimer dilinoleate, and (phytosteryl/isostearylketyl/stearyl/behenyl) dimer dilinoleate.

The dimer acid ester for use may be a commercially available product that is used in cosmetics, such as bis (behenyl/isostearyllphytosteryl) dimer dilinoleyl dimer dilinoleate sold under Plandool-G™ by Nippon Fine Chemical Co., Ltd., (phytosteryllisostearylketyl/stearyl/behenyl) dimer dilinoleate sold under Plandool-H™ by Nippon Seika Co., Ltd., bisstearyl dimer dilinoleyl dimer dilinoleate sold under LUSPLAN DA-DD-IS™ by Nippon Seika Co., Ltd., or hydrogenated castor oil dimer dilinoleate sold under RISOCAST DA-L™ by Kokyu Alcohol Industrial Co.

The dimer acid ester may be in a paste form at 25° C.

In one or more embodiments, a content of component (D) in the oily stick-shaped cosmetic may be 1% to 8% by mass, 2% to 7% by mass, or 2.5% to 4.8% by mass, based on a total amount of the oily stick-shaped cosmetic, from the viewpoint of close adhesiveness to the skin.

From the viewpoint of suppressing blooming and securing strength, a sum of contents of the component (A) and the component (D) may be 4% to 10% by mass, or 5% to 8% by mass, based on a total amount of the oily stick-shaped cosmetic.

From the viewpoint of suppressing blooming, a mass ratio between the component (A) and the component (D) [component (A)/component (D)] may be 1/6 to 1/1, or 1/4 to 1/2.

Other Oily Components

In one or more embodiments, the oily stick-shaped cosmetic may comprise other types of oil agents that are used in cosmetics as oily components in addition to, or in place of, one or more of the components (A) to (D), such as a solid oil or an oil agent other than the solid oil. The other oily component may be used alone, or two or more kinds thereof may be used in combination.

Examples of the solid oil include hydrocarbons such as paraffin wax, microcrystalline wax, and polyethylene; plant-derived oils and fats such as hardened castor oil (hydrogenated castor oil), hydrogenated jojoba oil, carnauba wax, and rice wax; esters such as glyceryl tribehenate and cholesterol fatty acid esters; higher alcohols such as stearyl alcohol and behenyl alcohol; silicones such as acryl-modified silicone; and sugar fatty acid esters such as dextrin palmitate and inulin stearate. The solid oil may be used alone, or two or more kinds thereof may be used in combination.

The oil agent other than the solid oil for use may be a paste-like oil or a liquid oil. Examples of the paste-like oil include petrolatum, dipentaerythrityl hexa(hydroxy stearate/stearate/rosinate), dipentaerythrityl tetra(hydroxy stearate/isostearate), dipentaerythrityl pentaisostearate, dipentaerythrityl hexahydroxystearate, glyceryl tri(caprylate/caprate/myristate/stearate), hydrogenated castor oil isostearate, phytosteryl oleate, sucrose hexa(oleate/palmitate/stearate), phytosteryl macadamiate, and bis-diglyceryl polyacyladipate-2.

Examples of the liquid oil include ester oils such as cetyl ethylhexanoate, ethylhexyl palmitate, triethylhexanoin, isotridecyl isononanoate, isostearyl isostearate, neopentyl glycol diethylhexanoate, glyceryl tri(caprylate-caprate), neopentyl glycol dicaprate, propanediol diisostearate, trimethylolpropane triethylhexanoate, octyl dodecyl myristsate, octyl dodecyl stearoyloxystearate, diisostearyl malate, polyglyceryl triisostearate, dipentaerythrityl pentaisostearate, and trimethylolpropane triisostearate; silicone oils such as dimethicone and methyl phenyl polysiloxane; hydrocarbon oils such as liquid paraffin, squalane, olefin oligomers, and hydrogenated polyisobutene; vegetable oils such as sunflower seed oil, jojoba seed oil, olive oil, and castor oil; and higher alcohols such as isostearyl alcohol, octyldodecanol, and oleyl alcohol.

In one or more embodiments, the oily stick-shaped cosmetic may comprise a hydrogenated castor oil, from the viewpoint of maintaining strength and enhancing stability. In some embodiments, a content of the hydrogenated castor oil may be 8% to 20% by mass, 10% to 15% by mass, or 10.5% to 12% by mass, based on a total amount of the oily stick-shaped cosmetic.

In one or more embodiments, a content of the ester oil other than the component (A) or the component (D) (hereinafter, also referred to as "other ester oil") in the oily stick-shaped cosmetic may be 1% to 10% by mass in some embodiments, or 3% to 9% by mass in other embodiments, based on a total amount of the oily stick-shaped cosmetic.

The other ester oil for use may be one having a viscosity at 25° C. of 5 to 30,000 mPa·s. The other ester oil may be used alone, or two or more kinds thereof may be used in combination.

The viscosity at 25° C. refers to a value obtained by measurement using a B-type viscometer at a temperature of 25° C. and a rotational speed of 12 rpm.

The other ester oil may comprise a high-viscosity ester oil having a viscosity at 25° C. of 10,000 to 30,000 mPa·s and a low-viscosity ester oil having a viscosity at 25° C. of 5 to 500 mPa·s for combined use.

In one or more embodiments, a content of the oily components in the oily stick-shaped cosmetic may be 35% to 65% by mass, 46% to 60% by mass, or 48% to 58% by mass, based on a total amount of the oily stick-shaped cosmetic.

Powder Component

The powder component may comprise an extender powder, a white pigment, a coloring pigment, and other types of powders used in cosmetics. The powder may take various shapes such as a spherical shape, a plate-like shape, or a needle-like shape, may have a particle size such as an aerosol-like size, a microparticulate size, or a pigment-grade size, and may have a particle structure such as a porous structure or a non-porous structure.

Example powders include extender pigments such as mica, synthetic mica, sericite, talc, kaolin, silicon carbide, barium sulfate, bentonite, smectite, aluminum oxide, silica, magnesium oxide, zirconium oxide, magnesium carbonate, calcium carbonate, chromium oxide, aluminum hydroxide, and magnesium hydroxide; ultraviolet scattering agents such as microparticulate titanium oxide and microparticulate zinc oxide; organic powders such as nylon powder, polymethyl methacrylate powder, acrylonitrile-methacrylic acid copolymer powder, vinylidene chloride-methacrylic acid copolymer, polyethylene powder, polystyrene powder, organopolysiloxane elastomer powder, polymethylsilsesquioxane powder, urethane powder, wool powder, silk powder, cellulose powder, and N-acyl lysine powder; composite powders such as microparticulate titanium oxide-coated titanated mica, microparticulate titanium oxide-coated nylon, barium sulfate-coated titanated mica, titanium oxide-containing silica, and zinc oxide-containing silica; and metal soaps such as magnesium stearate, zinc myristate, aluminum stearate, and calcium stearate.

Examples of the coloring pigment include inorganic coloring pigments such as red iron oxide, yellow iron oxide, black iron oxide, cobalt oxide, chromium oxide, ultramarine blue, Prussian blue, titanium oxide, and zinc oxide; organic coloring pigments such as Red No. 228, Red No. 226, Blue No. 404, Red No. 202, and Yellow No. 4 aluminum lakes; pearl pigments such as titanated mica, microparticulate titanium oxide-coated titanated mica, barium sulfate-coated titanated mica, fish scale guanine, bismuth oxychloride, and aluminum flakes; and natural colorants such as carmine and safflower.

These powder components may be hydrophobically treated powders, from the viewpoints of color development and close adhesiveness. The hydrophobic treatment may use higher fatty acids, metal soaps, fats and oils, waxes, silicone compounds, fluorine compounds, surfactants, and dextrin fatty acid esters.

The powder components may be used alone, or two or more kinds thereof may be used in combination.

In one or more embodiments, a content of the powder component in the oily stick-shaped cosmetic may be 35% to 65% by mass, 40% to 54% by mass, or 42% to 52% by mass, based on a total amount of the oily stick-shaped cosmetic.

In one or more embodiments, the oily stick-shaped cosmetic may comprise components in addition to those described above. Examples of the additional components that may be used include a surfactant, an antiseptic agent, an antioxidant, a colorant, a thickener, a pH adjusting agent, a fragrance, an ultraviolet absorber, an ultraviolet scattering agent, a chelating agent, an antiphlogistic agent, and a humectant.

In one or more embodiments, the oily stick-shaped cosmetic may be produced by following the example procedures mentioned here. The oily components and other optional components are mixed, and the mixture is heated and melted. The molten product thus obtained is mixed with the powder component, and the mixture is uniformly dispersed with a three-roll mill or a stirrer. Subsequently, this mixture (i.e., cosmetic base material) may be molded using an extrusion molding machine, a mold, or the like, and thereby, the oily stick-shaped cosmetic can be obtained.

The oily stick-shaped cosmetic may take various shapes. For example, the shape of a transverse cross-section of the oily stick-shaped cosmetic that orthogonally intersects its longitudinal direction may be a circle, an ellipse, a triangle, a rectangle, or a polygon with the number of its corners being 5 or more. Since the oily stick-shaped cosmetic can have suppressed blooming and improved storage stability, usability and strength all in a well-balanced manner, it can be satisfactorily and sufficiently used up even when it has a slender or a thin shape.

When the cross-sectional shape is a circle or an ellipse, the diameter or the shortest part diameter that passes through the center of the ellipse may be from 0.5 mm to 7 mm, and the lower limit may be 0.7 mm, 1 mm, or 1.3 mm, while the upper limit may be 5 mm, 3 mm, 2 mm, or 1.5 mm.

When the cross-sectional shape is a triangle, the height may be from 0.5 mm to 5 mm, and the lower limit may be 0.8 mm, 1 mm, or 1.5 mm, while the upper limit may be 4 mm, 3 mm, or 2 mm.

When the cross-sectional shape is a rectangle, the thickness in the minor axis direction may be from 0.4 mm to 2.0 mm. Furthermore, the lower limit of the thickness may be 0.6 mm, 0.7 mm, or 0.8 mm, while the upper limit of the thickness may be 0.9 mm or 1.5 mm.

The oily stick-shaped cosmetic may suitably be used as an eyebrow pencil, an eyeliner pencil, a lip liner, an eye color pencil, or concealer pencil. The oily stick-shaped cosmetic can also be used for a pencil type cosmetic product from which a stick-shaped cosmetic is projected for use.

ADDITIONAL EXAMPLES

It is to be understood that not all aspects, advantages and features described herein may necessarily be achieved by, or included in, any one particular example. Indeed, having described various examples herein, it should be apparent that other examples may be modified in arrangement and detail as per the following additional Examples, with reference to Tables 1-6. The numerical values in the tables represent contents (% by mass) based on the total amount of cosmetic base materials.

Prior to the description of the Examples, evaluation methods employed in each of the Examples will be described.

Blooming

Molded stick-shaped cosmetics were stored for 4 weeks under various temperature conditions (−5° C., 5° C., 25° C., 40° C., 50° C., and a cycle of from 5° C. to 40° C.). The states of the cosmetics after storage were visually inspected, and blooming was evaluated according to the following determination criteria.

[Determination Criteria]

A: Blooming was not observed.

B: Blooming was observed.

C: Pronounced blooming was observed.

Evaluation of Usability

A panel of 10 cosmetic evaluation experts were asked to use the respective samples of the oily stick-shaped cosmetics of the Examples and Comparative Examples, which had been stored for 4 weeks at 5° C. or which were before storage, to evaluate usability from the viewpoints of easy drawability (no sensation of being caught on the skin), no stickiness, and gentle touch on the skin. Evaluation of usability was carried out by performing a five-grade evaluation according to the following evaluation criteria, assigning a score for each of the samples. Further, averages of the scores from all the panel members are rated according to the following determination criteria.

[Scores: Evaluation Criteria]
5 points: Very good
4 points: Good
3 points: Fair
2 points: Slightly poor
1 point: Poor

[Determination Criteria (Average of Scores)]
A+: 4 or more
A: 3 or more and less than 4
B: 2 or more and less than 3
C: Less than 2

Evaluation of Storage Stability

Molded stick-shaped cosmetics were stored for 4 weeks at 50° C. The states of the cosmetics after storage were visually inspected, and storage stability was evaluated according to the following determination criteria. Evaluation was performed with N=2, and if the determination results were different, more negative determination results were employed.

[Determination Criteria]
A: Oil seepage was not observed.
C: Oil seepage was observed.

Evaluation of Drop Resistance

A sample of the oily stick-shaped cosmetic that had been stored for one week at 5° C. was dropped, immediately after being taken out, ten times from a height of 70 cm on a P tile in a direction parallel to a floor, and it was checked whether there was no core breakage. Evaluation was performed with N=5, among which a case where there was no core breakage in all dropped samples was rated as A, and a case where there was core breakage in at least one dropped sample was rated as C.

Evaluation of Breaking Strength

Molded stick-shaped cosmetics were stored for 4 weeks under various temperature conditions (−5° C., 5° C., 25° C., 40° C., 50° C., and a cycle of from 5° C. to 40° C.). The states of the cosmetics after storage were visually inspected, and blooming was evaluated according to the following determination criteria. For each of stick-shaped cosmetics before storage and after storage, a breaking load at the time of applying a load at a rate of 2 mm/min to the center of a core that was supported at an inter-fulcrum distance of 20 mm, was measured at 25° C. using a rheometer (manufactured by Fudo Kogyo K.K.). Measurements were made with N=5, and an average was determined. The breaking load of the stick-shaped cosmetic before storage was designated as an initial value, and the breaking strength was evaluated according to the following criteria on the basis of the difference of the breaking load of the stick-shaped cosmetic after storage relative to this initial value.

[Determination Criteria]
A: Difference from the initial value is less than ±20%.
B: Difference from the initial value is ±20% or more and less than ±30%.
C: Difference from the initial value is ±30% or more.

Moldability

The oily stick-shaped cosmetics were molded into cylindrical shapes each having a diameter of 1.5 mm with an extrusion molding machine, and the states of the materials were checked.
A: Molding without any problem.
C: Molding incomplete (noticeable bending, scratch, or breakage).

Examples 1 to 22 and Comparative Examples 1 to 4

Oily stick-shaped cosmetics (eyebrow pencils) having the compositions (% by mass) shown in Tables 1 to 3 were prepared by the method described below, and the above-described evaluations were carried out. Results are collectively presented in Tables 1 to 3.

Production Method

The powder components were admixed to a mixture obtained by melting the oily components at 80° C. to 100° C. and uniformly dispersed therein using a three-roll mill to obtain a cosmetic base material. The cosmetic base material thus obtained was molded into a cylindrical shape having a diameter of 1.5 mm with an extrusion molding machine.

TABLE 1

|  |  | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Oily component | Hydrogenated castor oil | 12.0 | 12.0 | 12.0 | 12.0 | 12.0 | 12.0 | 12.0 | 12.0 | 12.0 | 12.0 |
|  | Japan wax | 9.0 | 9.0 | 9.0 | 9.0 | 9.0 | 9.0 | 9.0 | 9.0 | 9.0 | 9.0 |
|  | Stearic acid | 18.0 | 18.0 | 18.0 | 18.0 | 18.0 | 18.0 | 18.0 | 18.0 | 18.0 | 18.0 |
|  | Partially hydrogenated jojoba ester A | 2.0 | — | — | 3.0 | 2.0 | 1.8 | 1.2 | 1.0 | 0.9 | 1.2 |
|  | Partially hydrogenated jojoba ester B | — | 2.0 | — | — | — | — | — | — | — | — |
|  | Partially hydrogenated jojoba ester C | — | — | 2.0 | — | — | — | — | — | — | — |
|  | Dimer acid ester A | 4.5 | 4.5 | 4.5 | 3.0 | 4.0 | 5.4 | 4.8 | 5.0 | 5.4 | 2.8 |
|  | Polyglyceryl-2 triisostearate | 4.0 | 4.0 | 4.0 | 4.0 | 4.0 | 4.0 | 4.0 | 4.0 | 4.0 | 4.0 |
|  | Trimethylolpropane triisostearate | 3.5 | 3.5 | 3.5 | 3.5 | 3.5 | 3.5 | 3.5 | 3.5 | 3.5 | 3.5 |
|  | Tocopherol | ≤0.1 | ≤0.1 | ≤0.1 | ≤0.1 | ≤0.1 | ≤0.1 | ≤0.1 | ≤0.1 | ≤0.1 | ≤0.1 |

TABLE 1-continued

|  |  | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Powder component | Synthetic fluorphlogopite | Balance | Balance | Balance | Balance | Balance | Balance | Balance | Balance | Balance | Balance |
|  | Black iron oxide | 7.5 | 7.5 | 7.6 | 7.5 | 7.5 | 7.5 | 7.5 | 7.5 | 7.5 | 7.5 |
|  | Yellow iron oxide | 5.5 | 5.5 | 5.7 | 5.5 | 5.5 | 5.5 | 5.5 | 5.5 | 5.5 | 5.5 |
|  | Titanium oxide | 10.0 | 10.0 | 11.1 | 10.0 | 10.0 | 10.0 | 10.0 | 10.0 | 10.0 | 10.0 |
|  | Red iron oxide | 4.0 | 4.0 | 4.0 | 4.0 | 4.0 | 4.0 | 4.0 | 4.0 | 4.0 | 4.0 |

TABLE 2

|  |  | Example 11 | Example 12 | Example 13 | Example 14 | Example 15 | Example 16 | Example 17 | Example 18 | Example 19 | Example 20 |
|---|---|---|---|---|---|---|---|---|---|---|---|
| Oily component | Hydrogenated castor oil | 12.0 | 12.0 | 12.0 | 12.0 | 11.0 | 12.0 | 8.0 | 10.5 | 10.0 | 12.0 |
|  | Japan wax | 9.0 | 9.0 | 9.0 | 9.0 | 11.0 | 15.0 | 6.0 | 6.0 | 15.0 | 9.0 |
|  | Stearic acid | 18.0 | 18.0 | — | 18.0 | 17.0 | 20.0 | 11.0 | 24.0 | 11.0 | 18.0 |
|  | Palmitic acid | — | — | 18.0 | — | — | — | — | — | — | — |
|  | Partially hydrogenated jojoba ester A | 2.5 | 3.1 | 2.0 | 2.0 | 2.0 | 3.1 | 2.5 | 2.5 | 3.0 | 2.0 |
|  | Dimer acid ester A | 5.5 | 6.9 | 4.5 | — | — | 6.9 | 4.5 | 4.5 | 5.4 | 4.5 |
|  | Dimer acid ester B | — | — | — | 4.5 | 3.0 | — | — | — | — | — |
|  | Polyglyceryl-2 triisostearate | 4.0 | 4.0 | 4.0 | 4.0 | 3.0 | 4.0 | 4.0 | 4.0 | 4.0 | — |
|  | Trimethylolpropane triisostearate | 3.5 | 3.5 | 3.5 | 3.5 | 3.48 | 3.5 | 3.5 | 3.5 | 3.5 | 7.5 |
|  | Tocopherol | ≤0.1 | ≤0.1 | ≤0.1 | ≤0.1 | ≤0.1 | ≤0.1 | ≤0.1 | ≤0.1 | ≤0.1 | ≤0.1 |
| Powder component | Synthetic fluorphlogopite | Balance | Balance | Balance | Balance | Balance | Balance | Balance | Balance | Balance | Balance |
|  | Black iron oxide | 7.5 | 7.5 | 7.6 | 7.6 | 23.3 | 7.6 | 7.6 | 7.6 | 7.6 | 7.5 |
|  | Yellow iron oxide | 5.5 | 5.5 | 5.7 | 5.7 | 7.2 | 5.7 | 5.7 | 5.7 | 5.7 | 5.5 |
|  | Titanium oxide | 10.0 | 10.0 | 11.1 | 11.1 | 1.7 | 11.1 | 11.1 | 11.1 | 11.1 | 10.0 |
|  | Red iron oxide | 4.0 | 4.0 | 4.0 | 4.0 | 7.0 | 4.0 | 4.0 | 4.0 | 4.0 | 4.0 |

TABLE 3

|  |  | Example 21 | Example 22 | Comparative Example 1 | Comparative Example 2 | Comparative Example 3 | Comparative Example 4 |
|---|---|---|---|---|---|---|---|
| Oily component | Hydrogenated castor oil | 12.0 | 12.0 | 12.0 | 12.0 | 12.0 | 12.0 |
|  | Japan wax | 9.0 | 9.0 | 9.0 | 9.0 | 9.0 | 9.0 |
|  | Stearic acid | 18.0 | 18.0 | 18.0 | 18.0 | 18.0 | 18.0 |
|  | Partially hydrogenated jojoba ester A | 2.0 | 2.0 | — | 2.0 | — | — |
|  | Hydrogenated jojoba oil | — | — | — | — | — | 2.0 |
|  | Dimer acid ester A | 4.5 | 4.5 | 4.5 | — | — | 4.5 |
|  | Polyglyceryl-2 triisostearate | — | — | 4.0 | 4.0 | 4.0 | 4.0 |
|  | Trimethylolpropane triisostearate | 7.5 | — | 3.5 | 3.5 | 3.5 | 3.5 |
|  | Ethylhexyl palmitate | — | 7.5 | — | — | — | — |
|  | Tocopherol | ≤0.1 | ≤0.1 | ≤0.1 | ≤0.1 | ≤0.1 | ≤0.1 |
| Powder component | Synthetic Fluorphlogopite | ≤0.1 | ≤0.1 | ≤0.1 | ≤0.1 | Balance | Balance |
|  | Black iron oxide | 5.5 | 5.5 | 7.6 | 7.6 | 7.6 | 7.6 |
|  | Yellow iron oxide | 10.0 | 10.0 | 5.7 | 5.7 | 5.7 | 5.7 |
|  | Titanium oxide | 4.0 | 4.0 | 11.1 | 11.1 | 11.1 | 11.1 |
|  | Red iron oxide | 5.5 | 5.5 | 4.0 | 4.0 | 4.0 | 4.0 |

TABLE 4

|  | Evaluation | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Blooming | After storage for 4 weeks at −5° C. | A | A | A | A | A | A | A | A | A | A |
|  | After storage for 4 weeks at 5° C. | A | A | A | A | A | A | A | A | A | A |
|  | After storage for 4 weeks at 25° C. | A | A | A | A | A | A | A | A | A | A |
|  | After storage for 4 weeks at 40° C. | A | A | A | A | A | A | A | A | A | A |
|  | After storage for 4 weeks at 50° C. | A | A | A | A | A | A | A | A | A | A |
|  | After storage for 4 weeks in a cycle of from 5° C. to 40° C. | A | A | A | A | A | A | A | A | A | A |

TABLE 4-continued

|  | Evaluation | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Storage stability | After storage for 4 weeks at 50° C. | A | A | A | A | A | A | A | A | A | A |
| Usability | Initial stage | A+ | A | A+ | A | A | A+ | A+ | A | A+ | A |
|  | After storage for 4 weeks at 5° C. | A+ | A | A+ | A | A | A+ | A+ | A | A+ | A |
| Breaking strength | Initial value (N) | 0.14 | 0.10 | 0.13 | 0.12 | 0.11 | 0.10 | 0.11 | 0.11 | 0.12 | 0.12 |
|  | After storage for 4 weeks at −5° C. | A | A | A | A | A | A | A | A | A | A |
|  | After storage for 4 weeks at 5° C. | A | A | A | A | A | A | A | A | A | A |
|  | After storage for 4 weeks at 25° C. | A | A | A | A | A | A | A | A | A |  |
|  | After storage for 4 weeks at 40° C. | A | A | A | A | A | A | A | A | A | A |
|  | After storage for 4 weeks at 50° C. | A | A | A | A | A | A | A | A | A | A |
|  | After storage for 4 weeks in a cycle of from 5° C. to 40° C. | A | A | A | A | A | A | A | A | A | A |
| Shatter strength | After storage for 1 week at 5° C. | A | A | A | A | A | A | A | A | A | A |
|  | Moldability | A | A | A | A | A | A | A | A | A | A |

TABLE 5

|  | Evaluation | Example 11 | Example 12 | Example 13 | Example 14 | Example 15 | Example 16 | Example 17 | Example 18 | Example 19 | Example 20 |
|---|---|---|---|---|---|---|---|---|---|---|---|
| Blooming | After storage for 4 weeks at −5° C. | A | A | A | A | A | A | A | A | A | A |
|  | After storage for 4 weeks at 5° C. | A | A | A | A | A | A | A | A | A | A |
|  | After storage for 4 weeks at 25° C. | A | A | A | A | A | A | A | A | A | A |
|  | After storage for 4 weeks at 40° C. | A | A | A | A | A | A | A | A | A | A |
|  | After storage for 4 weeks at 50° C. | A | A | A | A | A | A | A | A | A | A |
|  | After storage for 4 weeks in a cycle of from 5° C. and 40° C. | A | A | A | A | A | A | A | A | A | A |
| Storage stability | After storage for 4 weeks at 50° C. | A | A | A | A | A | A | A | A | A | A |
| Usability | Initial stage | A+ | A | A | A+ | A+ | A | A | A | A | A+ |
|  | After storage for 4 weeks at 5° C. | A+ | A | A | A+ | A+ | A | A | A | A | A+ |
| Breaking strength | Initial value (N) | 0.09 | 0.08 | 0.16 | 0.14 | 0.19 | 0.12 | 0.09 | 0.15 | 0.1 | 0.13 |
|  | After storage for 4 weeks at −5° C. | A | A | A | A | A | A | A | A | A | A |
|  | After storage for 4 weeks at 5° C. | A | A | A | A | A | A | A | A | A | A |
|  | After storage for 4 weeks at 25° C. | A | A | A | A | A | A | A | A | A |  |
|  | After storage for 4 weeks at 40° C. | A | A | A | A | A | A | A | A | A | A |
|  | After storage for 4 weeks at 50° C. | A | A | A | A | A | A | A | A | A | A |
|  | After storage for 4 weeks in a cycle of from 5° C. and 40° C. | A | A | A | A | A | A | A | A | A | A |
| Shatter strength | After storage for 1 week at 5° C. | A | A | A | A | A | A | A | A | A | A |
|  | Moldability | A | A | A | A | A | A | A | A | A | A |

TABLE 6

|  | Evaluation | Example 21 | Example 22 | Comparative Example 1 | Comparative Example 2 | Comparative Example 3 | Comparative Example 4 |
|---|---|---|---|---|---|---|---|
| Blooming | After storage for 4 weeks at −5° C. | A | A | A | A | A | A |
|  | After storage for 4 weeks at 5° C. | A | A | A | B | C | B |
|  | After storage for 4 weeks at 25° C. | A | A | B | B | C | B |
|  | After storage for 4 weeks at 40° C. | A | A | A | A | C | A |
|  | After storage for 4 weeks at 50° C. | A | A | A | A | A | A |
|  | After storage for 4 weeks in a cycle of from 5° C. and 40° C. | A | A | A | A | A | A |
| Storage stability | After storage for 4 weeks at 50° C. | A | A | A | A | C | A |
| Usability | Initial stage | A+ | A+ | B | B | A+ | C |
|  | After storage for 4 weeks at 5° C. | A+ | A+ | B | B | C | C |
| Breaking strength | Initial value (N) | 0.12 | 0.1 | 0.12 | 0.11 | 0.22 | 0.15 |
|  | After storage for 4 weeks at −5° C. | A | A | A | A | A | A |
|  | After storage for 4 weeks at 5° C. | A | A | A | B | B | A |
|  | After storage for 4 weeks at 25° C. | A | A | A | A | C | A |
|  | After storage for 4 weeks at 40° C. | A | A | A | A | A | A |
|  | After storage for 4 weeks at 50° C. | A | A | B | A | B | C |
|  | After storage for 4 weeks in a cycle of from 5° C. to 40° C. | A | A | A | A | A | A |
| Shatter strength | After storage for 1 week at 5° C. | A | A | A | C | A | A |
|  | Moldability | A | A | A | A | A | C |

In Tables 1 to 3, the details of the respective raw materials are as follows.

Partially hydrogenated jojoba ester A: sold under FLORAESTERS® 30 by International Flora Technologies, Ltd. (melting point of 52.6° C.)

Partially hydrogenated jojoba ester B: sold under FLORAESTERS® 20 by International Flora Technologies, Ltd. (melting point of 48.3° C.)

Partially hydrogenated jojoba ester C: sold under FLORAESTERS® 60 by International Flora Technologies, Ltd. (melting point of 58.9° C.)

Hydrogenated jojoba oil: sold under FLORAESTERS® 70 by International Flora Technologies, Ltd. (melting point of 70.3° C.)

Dimer acid ester A: phytosteryl/isostearylketyl/stearyl/behenyl dimer dilinoleate sold under Plandool-H™ by NIPPON FINE CHEMICAL CO., LTD.

Dimer acid ester B: bis(behenyl/isostearyl/phytosteryl) dimer dilinoleyl dimer dilinoleate) sold under Plandool-G™ by NIPPON FINE CHEMICAL CO., LTD.

Polyglyceryl-2 triisostearate having a viscosity 22,500 mPa·s at 25° C.

Trimethylolpropane triisostearate having a viscosity 180 mPa·s at 25° C.

Ethylhexyl palmitate having a viscosity 11 mPa·s at 25° C.

The above-described melting points were measured according to the following method.

About 5 mg of a sample was weighed and introduced into an aluminum sample pan. This pan was covered with an aluminum lid and was installed in a differential scanning calorimeter "DSC7020" (manufactured by Hitachi High-Tech Science Corporation, product name). The sample and a reference sample were maintained for 1 minute at −10° C. under a nitrogen gas at a flow rate of 30 to 35 mL/min using an electric cooling unit "POLYSCIENCE" (manufactured by Hitachi High-Tech Science Corporation, product name). Subsequently, a melting endothermic curve was obtained by raising the temperature from 0° C. to 120° C. at a rate of a temperature increase of 10° C./min, lowering the temperature from 120° C. to −10° C. at a rate of a temperature decrease of −10° C./min, maintaining the sample at −10° C. for 5 minutes, and then raising the temperature again from −10° C. to 120° C. at a rate of a temperature increase of 10° C./min. A peak temperature of the melting endothermic curve in the second temperature increase was designated as the melting point.

As shown in Tables 4 to 6, it was understood that in the eyebrow pencils of Examples 1 to 22, blooming was suppressed at various temperatures of −5° C. to 50° C. and under the conditions of a cycle of from 5° C. to 40° C., and at the same time, the eyebrow pencils had a combination of sufficient strength, storage stability, and usability. It was verified that the eyebrow pencils of Examples 1 to 22 could particularly achieve suppression of blooming in an actual use temperature range (5° C. to 25° C.) and storage stability at high temperatures in a well-balanced manner. Furthermore, it was found that the eyebrow pencils of Examples 1 to 22 retained satisfactory usability even after storage at 5° C. as well as stable breaking strength over a wide temperature range.

| Example 23 (Lip liner) | |
|---|---|
| | (Mixing proportion (mass %)) |
| (Oily component) | |
| Hydrogenated castor oil | 8.0 |
| Japan wax | 9.0 |
| Stearic acid | 12.0 |
| Partially hydrogenated jojoba ester A | 3.7 |
| Dimer acid ester B | 8.3 |
| Polyglyceryl-2 triisostearate | 6.0 |
| Trimethylolpropane triisostearate | 4.5 |
| Tocopherol | 0.1 |
| (Powder component) | |
| Synthetic fluorphlogopite | Balance |
| Black iron oxide | 4.0 |
| Yellow iron oxide | 0.10 |
| Titanium oxide | 6.0 |
| Red iron oxide | 0.10 |
| Red 202 | 8.50 |

The details of the above-described components are the same as those previously described.

Production Method

The oily components were stirred at 80° C. to 100° C., to which the powder components were mixed. A cosmetic base material was thus obtained. The obtained cosmetic base material was molded into a cylindrical shape having a diameter of 3 mm using an extrusion molding machine.

EVALUATION

The obtained lip liner was evaluated in manners that were similar to those described above. The blooming was rated as "A" under all the storage conditions, the usability was rated as "A+" both at the initial stage and after storage, the storage stability was rated as "A," and the drop resistance was rated as "A." The breaking strength was rated as "A" under all the storage conditions; and its initial value was 0.15 N. The moldability was rated as "A."

What is claimed is:

1. An oily stick-shaped cosmetic comprising:
    a component (A) including a partially hydrogenated jojoba ester;
    a component (B) including Japan wax;
    a component (C) including a fatty acid having a carbon chain length of 12 or more;
    a component (D) including a dimer acid ester; and
    a hydrogenated castor oil,
    wherein a sum of contents of the component (B) and the component (C) is 60% to 74% by mass based on a sum of contents of the hydrogenated castor oil, the component (B), and the component (C).

2. The oily stick-shaped cosmetic according to claim 1, wherein the component (A) has a melting point of 45° C. to 55° C.

3. The oily stick-shaped cosmetic according to claim 1, wherein a sum of contents of the component (A) and the component (D) is 4% to 10% by mass based on a total amount of the oily stick-shaped cosmetic.

4. The oily stick-shaped cosmetic according to claim 1, wherein a mass ratio between the component (A) and the component (D) [component (A)/component (D)] is 1/6 to 1/1.

5. The oily stick-shaped cosmetic according to claim 1, wherein a content of the hydrogenated castor oil is 8% to 20% by mass based on a total amount of the oily stick-shaped cosmetic.

6. The oily stick-shaped cosmetic according to claim 1, further comprising at least one oil agent selected from the group consisting of a solid oil, an oil paste, and a liquid oil.

7. The oily stick-shaped cosmetic according to claim 6, wherein the at least one oil agent is an ester oil other than the component (A) or the component (B) and a content of the ester oil is 1% to 10% by mass based on a total amount of the oily stick-shaped cosmetic.

8. The oily stick-shaped cosmetic according to claim 1, further comprising a powder component.

9. The oily stick-shaped cosmetic according to claim 8, wherein a content of the powder component is 35% to 65% by mass based on a total amount of the oily stick-shaped cosmetic.

\* \* \* \* \*